(12) United States Patent
Yarmush et al.

(10) Patent No.: US 8,993,328 B2
(45) Date of Patent: Mar. 31, 2015

(54) MEDIA CONDITIONING FOR IMPROVING GENE DELIVERY EFFICIENCY TO DIFFERENTIATING EMBRYONIC STEM CELLS

(75) Inventors: Martin L. Yarmush, Piscataway, NJ (US); Eric J. Wallenstein, Morris Plains, NJ (US); Rene S. Schloss, East Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 541 days.

(21) Appl. No.: 12/564,903

(22) Filed: Sep. 22, 2009

(65) Prior Publication Data

US 2010/0184226 A1  Jul. 22, 2010

Related U.S. Application Data

(60) Provisional application No. 61/099,007, filed on Sep. 22, 2008.

(51) Int. Cl.
| | | |
|---|---|---|
| C12N 15/00 | (2006.01) | |
| C12N 5/00 | (2006.01) | |
| C12N 5/02 | (2006.01) | |
| C12N 5/07 | (2010.01) | |
| C12N 5/10 | (2006.01) | |
| C12N 15/87 | (2006.01) | |

(52) U.S. Cl.
CPC ..................... *C12N 15/87* (2013.01)
USPC ............ 435/455; 435/325; 435/354; 435/366

(58) Field of Classification Search
None
See application file for complete search history.

(56) References Cited

U.S. PATENT DOCUMENTS

| | | | | |
|---|---|---|---|---|
| 7,566,535 | B2 * | 7/2009 | Kmiec et al. | 435/6.16 |
| 7,683,236 | B2 * | 3/2010 | Boiani et al. | 800/24 |
| 2003/0135872 | A1 * | 7/2003 | Burgess et al. | 800/8 |
| 2006/0172414 | A1 * | 8/2006 | Weissman et al. | 435/354 |
| 2007/0218514 | A1 * | 9/2007 | Smith et al. | 435/7.24 |

OTHER PUBLICATIONS http://en.wikipedia.org/wiki/Gene_expression_profiling, No Author listed, no volume, no issue, no pages listed, no year listed. 1 page long.*
Wallenstein, et al. (2010) "Serum Starvation Improves Transient Transfection Efficiency in Differentiating Embryonic Stem Cells", Biotechnological Progress, 26: 1714-23.*
http://www.newscientist.com/article/dn7864-cord-blood-yields-ethical-embryonic-stem-cells.html, downloaded Apr. 10, 2012. Published Aug. 18, 2005 by Andy Coghlan. "Cord Blood Yeilds 'ethical' embronic stem cells", The New Scientist. No volume or issue number. No pages listed. 1 page long.*
Song, et al. (2004) "Electric Field-Induced Molecular Vibration for Noninvastive, Hig-Efficiency DNA Transfection", Molecular Therapy, 9(4): 607-616.*
http://en.wikipedia.org/wiki/Transfection, 2013 downloaded, no journal, no volume, no issue, no author, pp. 1-6.*
http://www.altogen.com/transfection_methods.php, 2013 downloaded, no journal, no volume, no issue, no author, pp. 1-2.*
http://en.wikipedia.org/wiki/Mammal, 2013 downloaded, no journal, no volume, no issue, no author, p. 1.*
http://en.wikipedia.org/wiki/Vertebrate, 2013 downloaded, no journal, no volume, no issue, no author, pp. 1-2.*
http://en.wikipedia.org/wiki/Invertebrate, 2013 downloaded, no journal, no volume, no issue, no author, p. 1.*
http://en.wikipedia.org/wiki/Muroid, 2013 downloaded, no journal, no volume, no issue, no author, pp. 1-2.*
Maguire, T., et al., "Control of Hepatic Differentiation Via Cellular Aggregation in an Alginate Microenvironment", Biotechnol Bioeng. Oct. 15, 2007;98(3):631-44.
Sharma, NS., et al., "Sodium Butyrate-treated Embryonic Stem Cells Yield Hepatocyte-like Cells Expressing a Glycolytic Phenotype", Biotechnol Bioeng. Aug. 20, 2006;94(6):1053-63.
Kiprilov et al., "Human embryonic stem cells in culture possess primary cilia with hedgehog signaling machinery," The Journal of Cell Biology (2008): 180:897-904.
Potier et al., "Prolonged hypoxia concomitant with serum deprivation induces massive human mesenchymal stem cell death," Tissue Engineering (2007) 13:(6):1325-1331.
Roitbak et al., "Neural stem/progenitor cells promote endothelial cell morphogenesis and protect endothelial cells against ischemia via HIF-1a-regulated VEGF signaling," J. Cereb Blood Flow Metab. (2008) 29(9):1530-1542.
Friedman et al., "Resistance to p53-mediated growth arrest and apoptosis in Hep 38 hepatoma cells", Oncogene (1997) 15, pp. 63-70.
Hultgårdh-Nilsson et al., Endogenous activation of c-myc expression and DNA synthesis in serum-starved neonatal rat smooth muscle cells, Differentiation (1993) 52: pp. 161-168.
Machesky et al., "Role of Actin Polymerization and Adhesion to Extracellular Matrix in Rao-and Rho-induced Cytoskeletal Reorganization", The Journal of Cell Biology, vol. 138, No. 4, Aug. 25, 1997 913-926.
Retta at al., "Focal Adhesion and Stress Fiber Formation Is Regulated by Tyrosine Phosphatase Activity", Experimental Cell Research 229, 307-317 (1996).
Murray et al., "Substrate stiffness regulates solubility of cellular vimentin", Molecular Biology of the Cell, vol. 25 Jan. 1, 2014.
Galardi-Castilla et al., "Srfb, a member of the Serum Response Factor family of transcription factors, regulates starvation response and early development in Dictyostelium", Developmental Biology 316 (2008) 260-274.

* cited by examiner

*Primary Examiner* — Robert M Kelly
(74) *Attorney, Agent, or Firm* — Fox Rothschild LLP; Gerard P. Norton; J. Eric Summer

(57) ABSTRACT

The present invention provides systems and methods for improving the efficiency of a transient gene delivery system to differentiating embryonic stem (ES) cells by serum starving the targeted cells for one to three days prior to transfection. Such a serum starvation surprisingly resulted in increased expression of a constitutively-controlled plasmid from 50.4% to 83.2% of the population and increased expression of a promoter/enhancer controlled plasmid from ~1.4% to ~3.7% of the population.

5 Claims, 9 Drawing Sheets

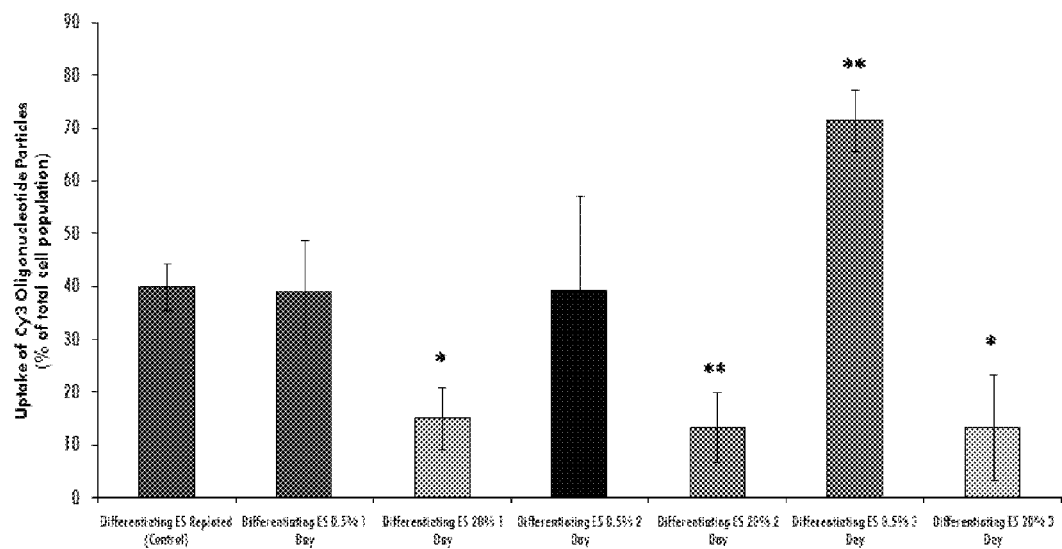

Figure 5:
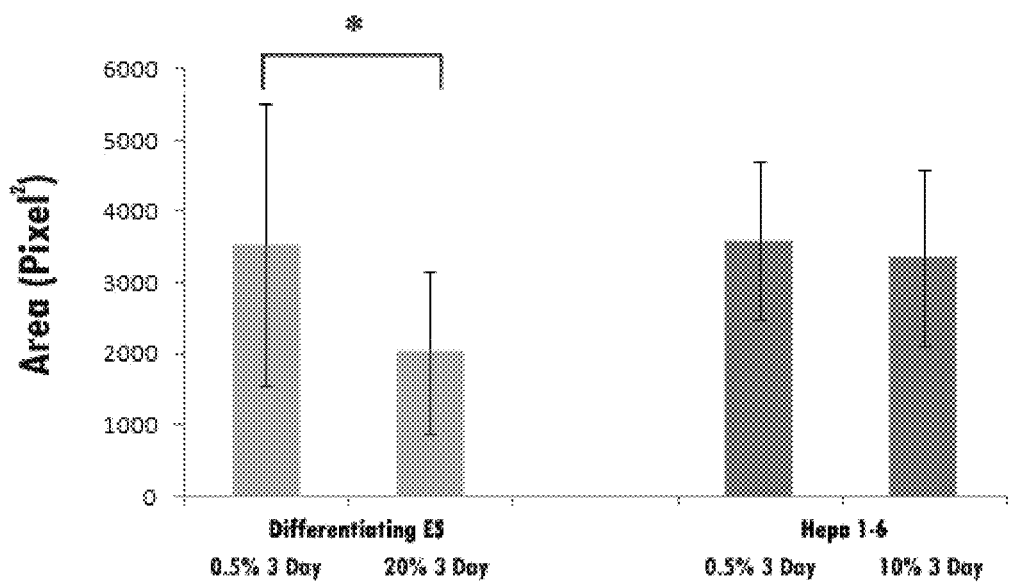

Figure 1. DNA uptake of Cy3 oligonucleotide lipoplexes. Uptake was determined via flow cytometry as the percentage of positively fluorescent cells at each time point. Solid lines represent cell conditions treated with 0.5% FBS-containing media for 1-3 days. Dashed lines represent cell conditions treated with normal 20% FBS-containing media for 1-3 days. Dotted line represents the replated cell control population.

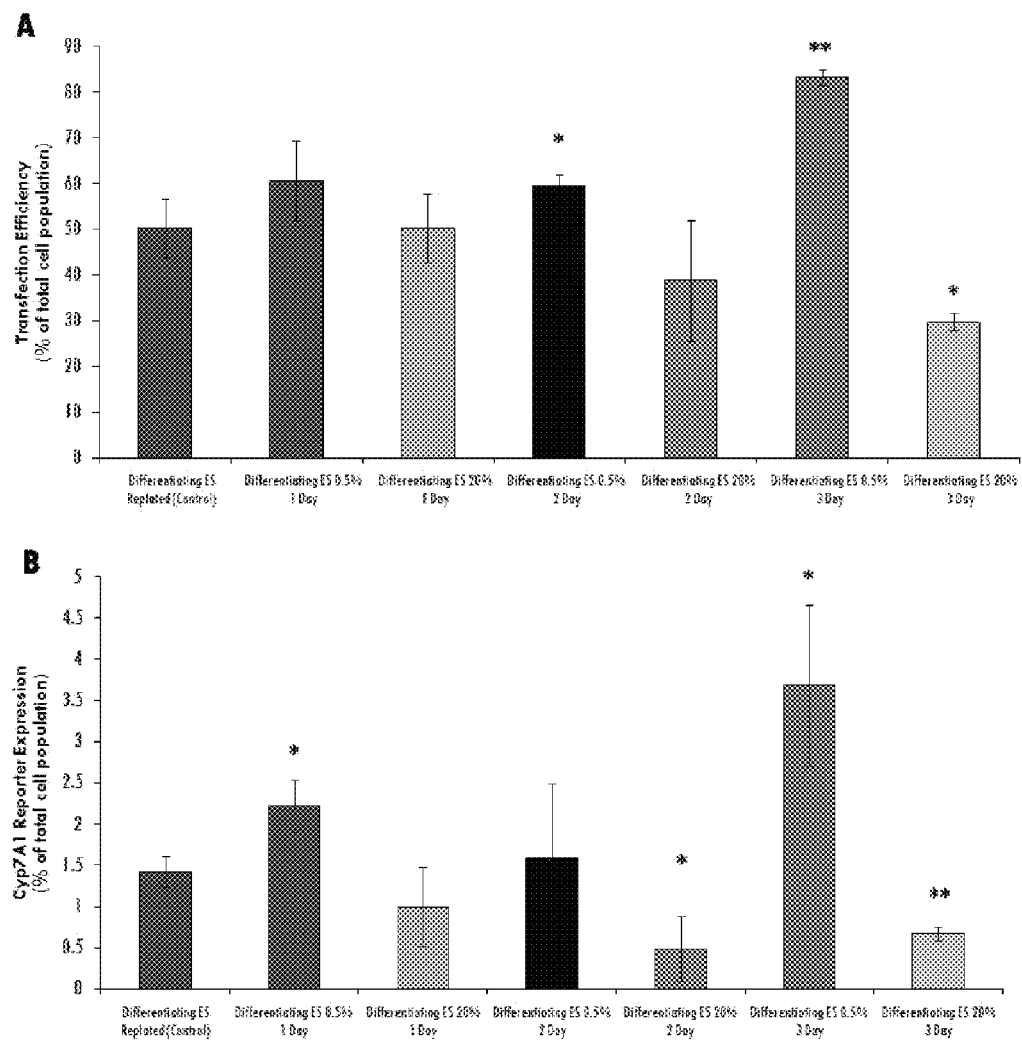

Figure 2. Transfection efficiency of media-conditioned differentiating ES cells. A: Expression of the constitutively-expressed CMV fluorescent plasmid for each treatment duration was measured via flow cytometry as the percentage of positively fluorescent cells 48 h after transfection. B: Expression of the liver-specific Cyp7A1 fluorescent plasmid for each treatment duration was measured via flow cytometry as the percentage of positively fluorescent cells 48 h after transfection.

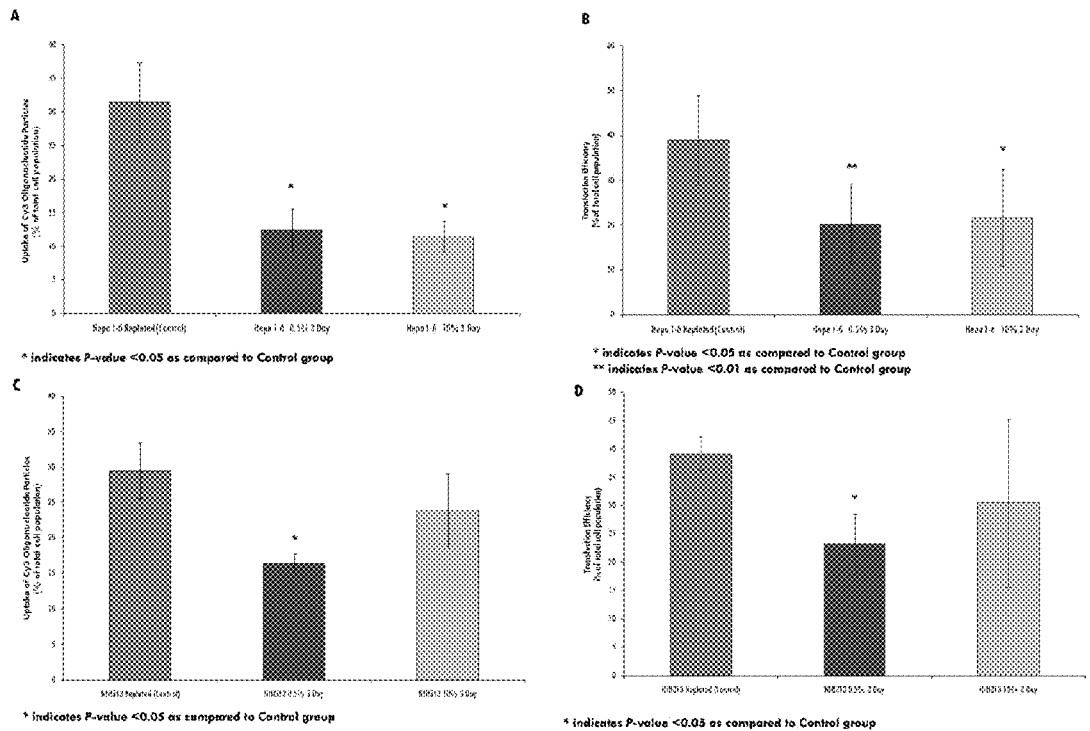

Figure 3. Effect of serum starvation on two other cell types: Hepa 1-6 hepatoma and NIH3T3 fibroblasts. A: Cy3 oligonucleotide uptake rates in control Hepa 1-6 replated cells (dotted line), Hepa 1-6 cells treated with 0.5% FBS-containing media for 3 days (solid line), and Hepa 1-6 cells treated with 10% FBS-containing media for 3 days (dashed line). B: Transfection efficiency was assessed by quantifying expression of the constitutively-expressed CMV fluorescent plasmid in control Hepa 1-6 replated cells, Hepa 1-6 cells treated with 0.5% FBS-containing media for 3 days, and Hepa 1-6 cells treated with 10% FBS-containing media for 3 days. C: Cy3 oligonucleotide uptake rates in control NIH3T3 replated cells (dotted line), NIH3T3 cells treated with 0.5% FBS-containing media for 3 days (solid line), and NIH3T3 cells treated with 10% FBS-containing media for 3 days (dashed line). D: Transfection efficiency was assess by quantifying expression of the constitutively-expressed CMV fluorescent plasmid in control NIH3T3 replated cells, NIH3T3 cells treated with 0.5% FBS-containing media for 3 days, and NIH3T3 cells treated with 10% FBS-containing media for 3 days.

A. Differentiating ES Replated (Control)
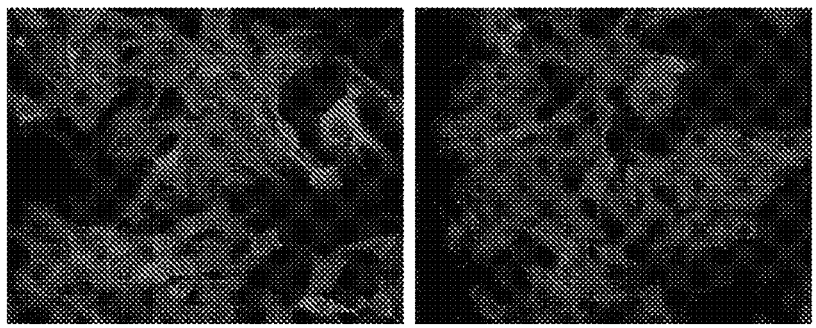
B. Differentiating ES 0.5% 3 Day
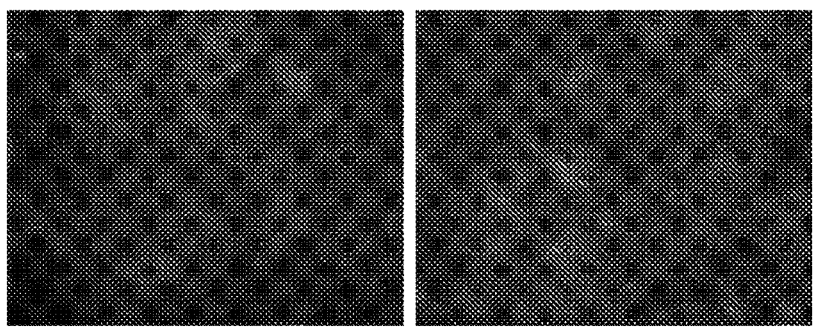
C. Differentiating ES 0.5% 3 Day post 10 min Transfection with Cy3 Oligonucleotides
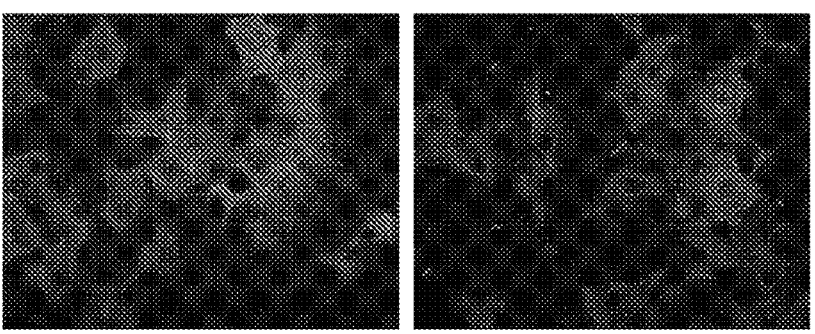
D. Differentiating ES 20% 3 Day
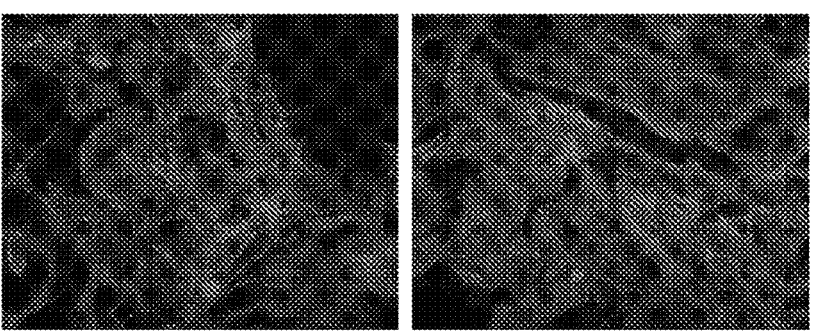
FIG. 4

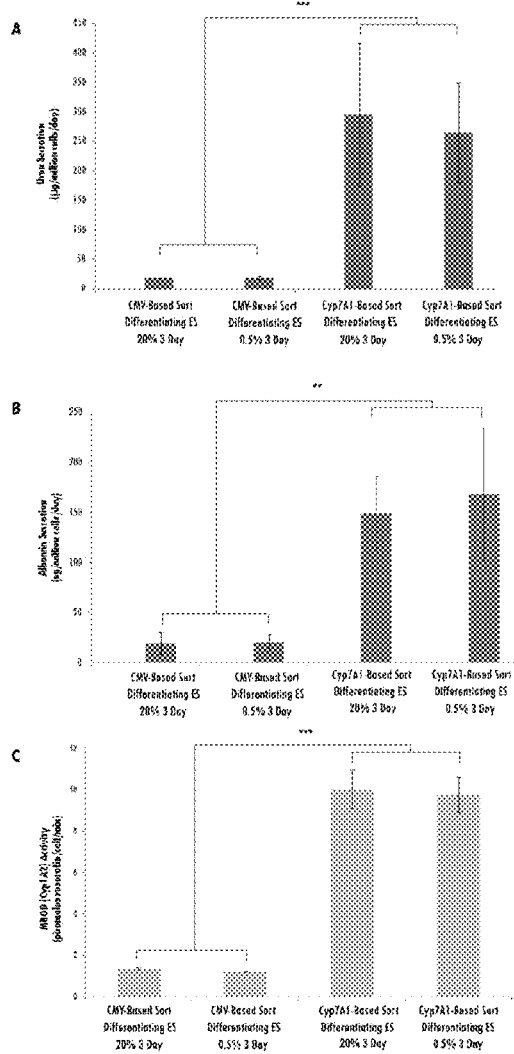

Figure 8. Functional assessment of sorted serum-starved and non serum-starved cells. A: Urea secretion of CMV-based and Cyp7A1-based sorted cells after three days of serum starvation (0.5% FBS) or normal media (20% FBS) treatment of differentiating ES cells. Urea secretion was detected using a colorimetric assay. B: Albumin secretion of CMV-based and Cyp7A1-based sorted cells after three days of serum starvation (0.5% FBS) or normal media (20% FBS) treatment of differentiating ES cells. Albumin secretion was detected using a sandwich ELISA. C: Cytochrome P450 1A2 detoxification activity of CMV-based and Cyp7A1-based sorted cells after three days of serum starvation (0.5% FBS) or normal media (20% FBS) treatment of differentiating ES cells. Cytochrome P450 activity was determined by measuring the formation of resorufin due to the activity of the isoenzyme methoxyresorufin-$O$-dealkylase (MROD, Cytochrome P450 1A2).

MEDIA CONDITIONING FOR IMPROVING GENE DELIVERY EFFICIENCY TO DIFFERENTIATING EMBRYONIC STEM CELLS

CROSS-REFERENCE TO RELATED APPLICATION

The instant application claims 35 U.S.C. §119(e) priority to U.S. Provisional Patent Application Ser. No. 61/099,007 filed Sep. 22, 2008, the disclosure of which is incorporated herein by reference.

STATEMENT REGARDING FEDERALLY SPONSORED RESEARCH OR DEVELOPMENT

The invention described herein was supported in whole or in part by grants from The National Institute of Health (Grant Nos. 5 R01 AI063795-02) and the National Science Foundation (Grant No. QSB 042496). The government has certain rights in the invention.

FIELD OF THE INVENTION

The present invention relates to systems and methods for improving the uptake and use of bioactive agents contained within a plasmid vector by culturing target cells in a serum starved condition.

BACKGROUND OF THE INVENTION

Genetic control of cell behavior is a critical issue in the field of stem biology, where determining a cell fate or reprogramming adult somatic cells into pluripotent cells has become a common experimental practice. Despite scientific advances in the field, in order for these cells to have therapeutic clinical potential techniques for controlling gene expression need to be developed that minimize or eliminate the risk of oncogenesis and mutagenesis. Possible routes for achieving this outcome could come in the form of a transient non-viral gene delivery system or through the addition of small chemical molecules.

The efficient delivery of DNA using non-viral plasmid vectors has been a major challenge in the fields of gene therapy, stem cell research, cellular therapeutics and RNAi/oncology (Bleiziffer et al., 2007; Clements et al., 2007; Dalby et al., 2004; Goessler et al., 2006; Šarić and Hescheler, 2008). Over the past decade, novel engineered materials have been developed along with quantitative physical characterization assays in an attempt to meet the highly efficient transduction capacity of viral vectors, such as retroviral and lentiviral systems, while maintaining a high level of safety, minimal toxicity, robustness for scale-up and the ability to carry large cargo (Clements et al., 2007; Douglas et al., 2006; Douglas, 2008; Douglas et al., 2008; Tsai et al., 2002). Recently, a transient gene delivery system was developed to deliver two fluorescent liver-specific reporter plasmids into differentiating, semi-mature murine embryonic stem (ES) cells for enriching a sub-population of hepatocyte-like cells (Wallenstein et al., 2008). The benefit of the transient expression of the plasmids fulfilled the system's needs, as the activation of the fluorescent reporters was only necessary prior to the completion of the cell sort. Despite the proof-of-concept of this concept, it was still limited by inherent low transfection efficiency (maximum≈56%) of plasmid expression. Improving the transfection efficiency to this population could dramatically improve the targeting of smaller subpopulations of cells to attain better sensitivity of expression values and to improve the recovery fraction. Recently, many groups have targeted adult somatic cells to generate induced pluripotent stem (iPS) cells by using retroviral vectors to express genes associated with pluripotency (Hanna et al., 2007; Meissner et al., 2007; Stadtfeld et al., 2008). Despite the success of these techniques, in order to realize the therapeutic potential of these cells in the future, the authors point out the need to develop alternate delivery methods that would minimize the risk of oncogenesis due to the random insertion of genes (Liu, 2008; Pera and Hasegawa, 2008). Such an approach may take the form of a transient gene delivery system or the use of small chemical molecules.

SUMMARY OF THE INVENTION

The present invention uses serum starvation to improve non-viral gene delivery (i.e., transfection) to mammalian cells, with a particular focus on differentiating embryonic stem (ES) cells. Serum starvation, the dramatic deprivation of normal levels of serum in media, is a cell culture technique used in a variety of applications, including cell cycle synchronization at the $G_0/G_1$ phase, reduction of cellular activities to basal levels by inactivating growth factor-stimulated kinases and the induction of quiescence and/or apoptosis (Coquelle et al., 2006; Golzio et al., 2002; Yu et al., 2006). Different cell types respond differently, if at all, to the degree and length of serum starvation (Oya et al., 2003). The serum deprivation response gene (SDR or SDPR) is expressed in serum-starved cells and is believed to be activated in a pathway distinct from cell-cell contact inhibition (Gustincich and Schneider, 1993; Gustincich et al., 1999).

With the foregoing in mind, and initially using a Cy3-tagged 20-mer oligonucleotide as a model of DNA uptake, the present invention assesses delivery trends and relates uptake to the transfection efficiency of a non-viral plasmid. The highest levels of transfection efficiency were surprisingly found after three days of serum starvation. In earlier work, it was found that sorting of differentiated ES cells driven by the liver-specific cytochrome P450 7α1 (Cyp7A1) promoter is more enriched in terms of albumin and urea secretion and cytochrome P450 1A2 (Cyp1A2) activity than cells sorted with a more ubiquitous reporter, driven by the albumin enhancer/promoter (Wallenstein et al., 2008). In the present invention, however, liver-specific cells were targeted using the Cyp7A1 reporter and found that serum starvation for three days significantly improves expression of this reporter as well. The Cy3 oligonucleotide model proved to be a simple system which enabled reasonable accuracy in predicting long-term transfection efficiency. Through several functional assays, serum starvation was determined not to disrupt the integrity of the cells.

DETAILED DESCRIPTION OF THE DRAWINGS

FIG. 1 illustrates DNA uptake of Cy3 oligonucleotide lipoplexes. Uptake was determined via flow cytometry as the percentage of positively fluorescent cells at each time point.

FIG. 2 illustrates transfection efficiency of media-conditioned differentiating ES cells. A: Expression of the constitutively-expressed CMV fluorescent plasmid for each treatment duration was measured via flow cytometry as the percentage of positively fluorescent cells 48 h after transfection. B: Expression of the liver-specific Cyp7A1 fluorescent plasmid for each treatment duration was measured via flow cytometry as the percentage of positively fluorescent cells 48 h after transfection.

FIG. 3 illustrates effect of serum starvation on two other cell types: Hepa 1-6 hepatoma and NIH3T3 fibroblasts. A: Cy3 oligonucleotide uptake rates in control Hepa 1-6 replated cells (dotted line), Hepa 1-6 cells treated with 0.5% FBS-containing media for 3 days (solid line), and Hepa 1-6 cells treated with 10% FBS-containing media for 3 days (dashed line). B: Transfection efficiency was assessed by quantifying expression of the constitutively-expressed CMV fluorescent plasmid in control Hepa 1-6 replated cells, Hepa 1-6 cells treated with 0.5% FBS-containing media for 3 days, and Hepa 1-6 cells treated with 10% FBS-containing media for 3 days. C: Cy3 oligonucleotide uptake rates in control NIH3T3 replated cells (dotted line), NIH3T3 cells treated with 0.5% FBS-containing media for 3 days (solid line), and NIH3T3 cells treated with 10% FBS-containing media for 3 days (dashed line). D: Transfection efficiency was assess by quantifying expression of the constitutively-expressed CMV fluorescent plasmid in control NIH3T3 replated cells, NIH3T3 cells treated with 0.5% FBS-containing media for 3 days, and NIH3T3 cells treated with 10% FBS-containing media for 3 days.

FIG. 4 illustrates F-actin staining of media-conditioned differentiating ES cells was performed using a rhodamine-phalloidin visualization kit on fixed cells. A: Differentiating ES cells replated for 4-12 h prior to fixation and staining. B: Differentiating ES cells serum-starved for 3 days prior to fixation and staining. C: Differentiating ES cells serum-starved for 3 days and transfected with Cy3 oligonucleotides for 10 min prior to fixation and staining. D. Differentiating ES cells treated with normal media for 3 days prior to fixation and staining.

FIG. 5 illustrates quantification of cell area of serum-starved (0.5% FBS) and non serum-starved (20% FBS for differentiating ES and 10% FBS for Hepa 1-6) cells after 3 days. Cells were fixed and stained for F-actin to aid in identifying distinct cell regions. Cell areas were then quantified as pixel$^2$ using Olympus Microsuite™ software.

Figure 6:
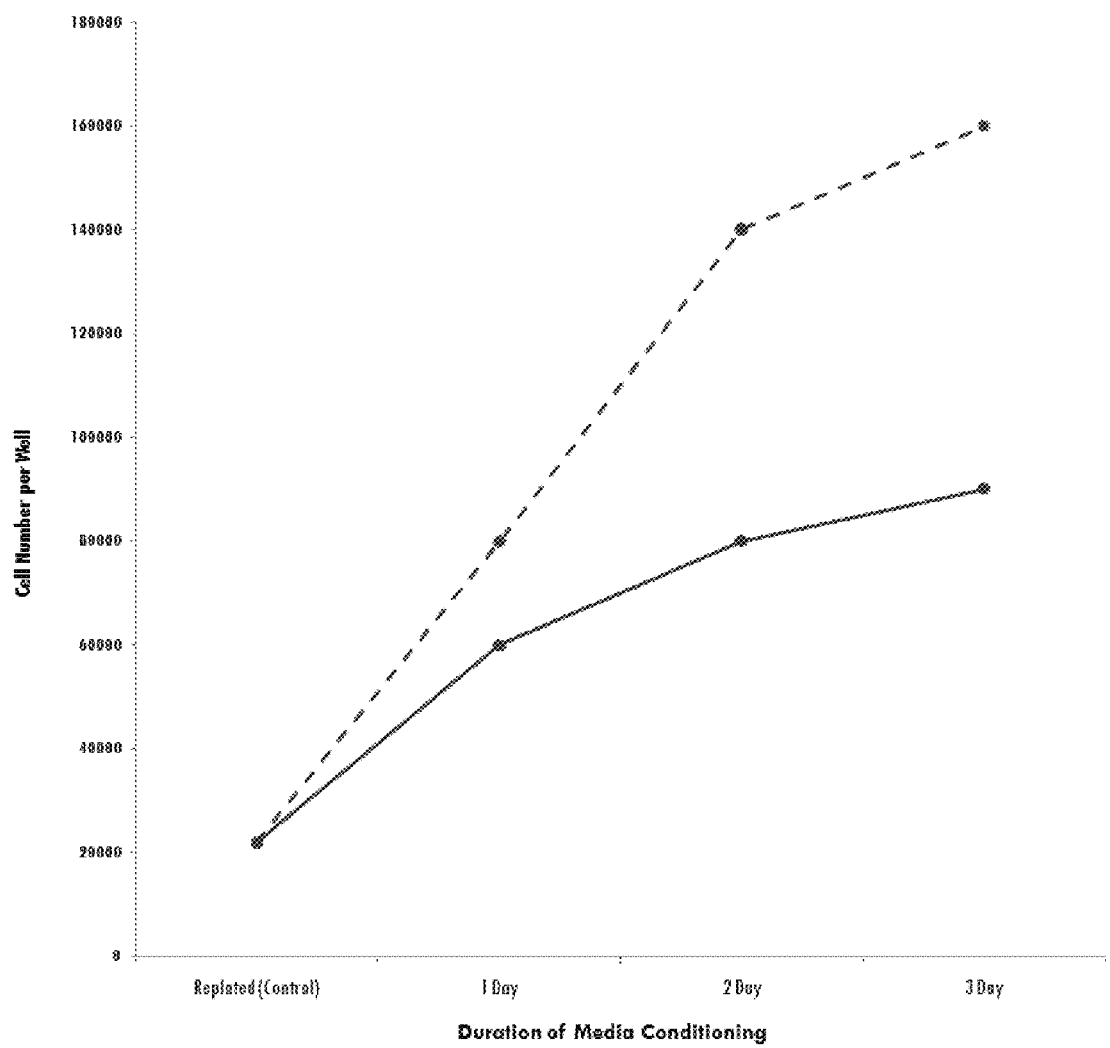

FIG. 6 illustrates cell proliferation of media-conditioned differentiating ES cells. Day 17 differentiating ES cells were uniformly plated into a 12-well plate. After 6 h, media was replenished with either 0.5% FBS-containing media or 20% FBS-containing media for an additional 1-3 days. Cells were quantified after trypsinization via Trypan blue exclusion. The solid line represents the serum-starved cells (20% FBS). The dashed line represents the non serum-starved cells (0.5% FBS).

Figure 7:
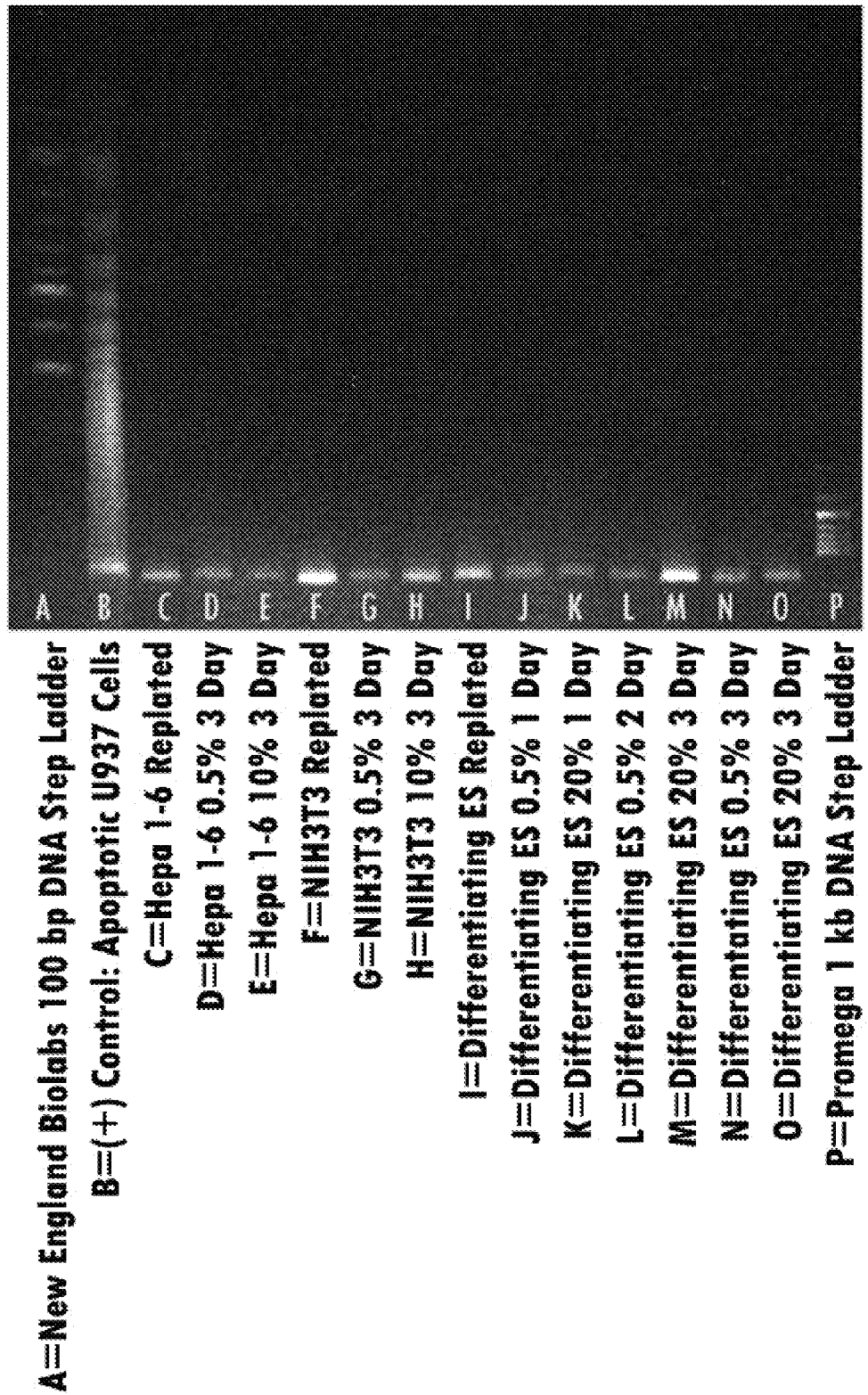

FIG. 7 illustrates detection of fragmented DNA in apoptotic or necrotic cells. Genomic DNA from all media-conditioned and replated cells studied (lanes C-O) was extracted and run via gel electrophoresis to detect for apoptosis (step band) or necrosis (smeared band). A positive control (lane B) is indicative of apoptotic activity. Lanes A and B are 100 by and 1 kb DNA step ladders, respectively.

FIG. 8 illustrates functional assessment of sorted serum-starved and non serum-starved cells. A: Urea secretion of CMV-based and C 7A1-based sorted cells after three days of serum starvation (0.5% FBS) or normal media (20% FBS) treatment of differentiating ES cells. Urea secretion was detected using a calorimetric assay. B: Albumin secretion of CMV-based and Cyp7A1-based sorted cells after three days of serum starvation (0.5% FBS) or normal media (20% FBS) treatment of differentiating ES cells. Albumin secretion was detected using a sandwich ELISA. C: Cytochrome P450 1A2 detoxification activity of CMV-based and Cyp7A1-based sorted cells after three days of serum starvation (0.5% FBS) or normal media (20% FBS) treatment of differentiating ES cells. Cytochrome P450 activity was determined by measuring the formation of resorufin due to the activity of the isoenzyme methoxyresorufin-O-dealkylase (MROD, Cytochrome P450 1A2).

Figure 9:
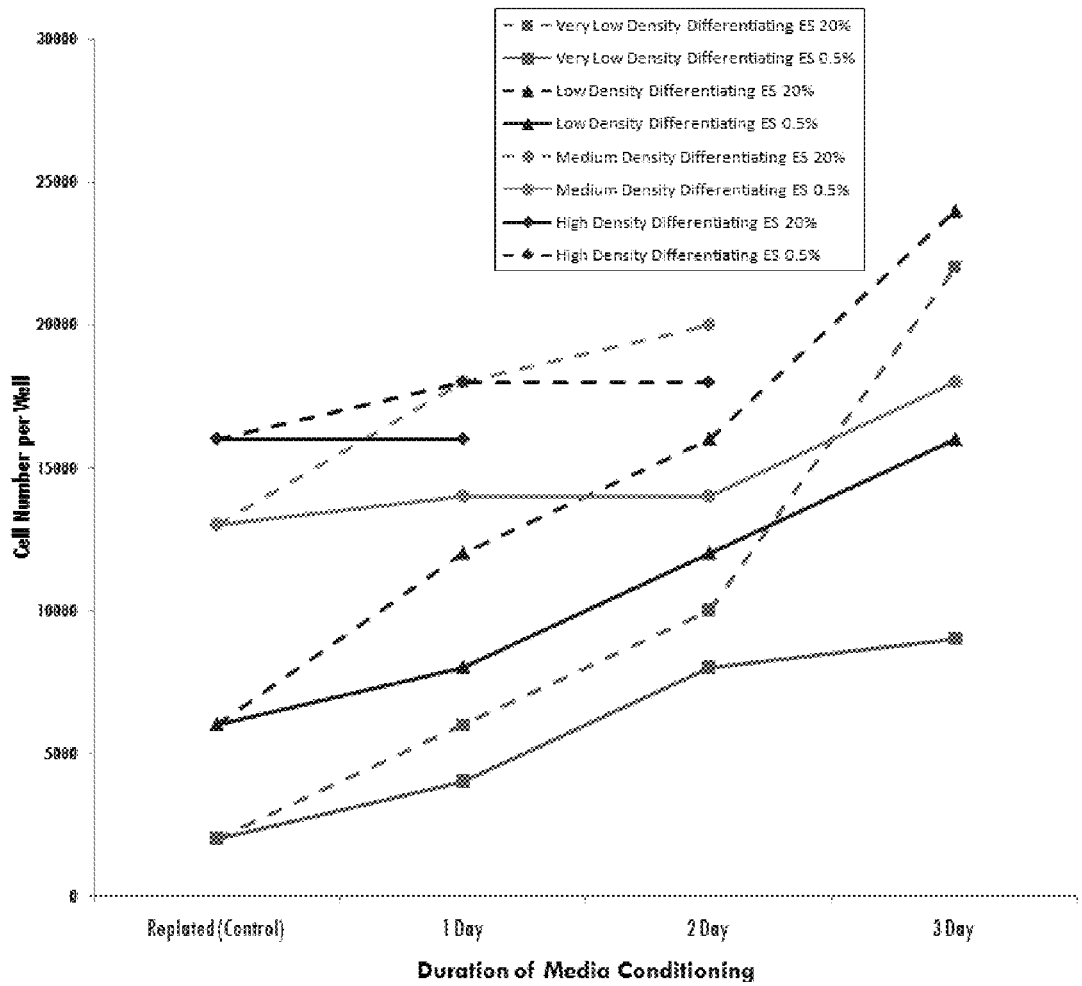

FIG. 9 illustrates cell proliferation of media-conditioned differentiating ES cells seeded at different starting densities to conserve uniform transfection conditions. Day 17 differentiating ES cells were plated into a 48-well plate at very low, low, medium and high densities. After 6 h, media was replenished with either 0.5% FBS-containing media or 200 FBS-containing media for an additional 1-3 days. Cells were quantified after trypsinization via Trypan blue exclusion. Plates were selected so that the cells in each well were in the 7000-22,000 range at the time of transfection. The solid lines represent the serum-starved cells. The dashed lines represent the non serum-starved cells.

DETAILED DESCRIPTION OF THE INVENTION

For purposes of the present invention, the effect that serum starvation has on improving nucleic acid delivery efficiency to differentiating ES cells is illustrated using a reproducible, rapid and inexpensive uptake model with which DNA delivery trends are quantified. This was first accomplished using a Cy3-linked 20-mer oligonucleotide. Physicoelectrical characterization of the DNA lipoplexes revealed slight differences between the plasmid DNA and the Cy3 oligonucleotide complexes. The Cy3 oligonucleotides were transfected with Lipofectamine™ 2000, and the uptake of the lipoplex particles quantified via flow cytometry after 12 min. The initial time point was chosen to permit the settling and concentration of the lipoplex particles closer to the cell surface (Luo and Saltzman, 2000). Results indicated that the serum-starved differentiating ES cells, as a whole, showed significantly higher Cy3 oligonucleotide uptake rates than their normal media-treated counterparts (with the highest rate occurring after three days). This trend paralleled the plasmid transfection efficiencies for expression of both the CMV- and Cyp7A1-driven plasmids, thus demonstrating the utility of the Cy3 oligonucleotide model to predict at an early time point the expression of plasmid DNA assessed after 48 hours.

Next, by reducing the levels of serum from 20% to 0.5% in the media of EB-mediated differentiating ES cells upon monolayer plating for three days, a significant increase in the percentage of transfected cells was achieved with a CMV-driven fluorescent reporter vector. The increase garnered by the serum-starved media also translated into a significant increase in the percentage of cells expressing a liver-specific Cyp7A1 fluorescent reporter vector. Both groups showed the greatest enhancement after three days of serum starvation. The specific three days of time for the differentiating ES cells but not the Hepa 1-6 or NIH3T3 cells may be due to a variety of factors idiosyncratic to other stem, highly proliferative or transformed cells, including growth rate and metabolic activity, resistance to serum starvation, demand and depletion of nutrients in the media, ability to respond to stress and the activation of the serum deprivation response gene (Gustinich and Schneider, 1993; Kim et al., 2002; Park et al., 2004; Schratt et al., 2001).

As it was determined in previous work by our group that transfection efficiency improves with less confluency, we ensured control of this factor at each time point of transfection by using wells initially seeded at different densities. Both the CMV- and Cyp7A1-transfected cells were sorted based on fluorescent reporter expression, and it was found that the serum starvation media did not alter the functional capacity of either group, when compared to cells treated with normal 20% FBS-containing media. Furthermore, there was negligible cell loss within the three days of media conditioning and no group showed signs of necrosis or apoptosis. As typical cell culture protocols call for the changing of media every 2-3 days, we do not find the 3-day serum starvation conditioning time period to be impractical. However, a better understanding of the mechanisms by which serum starvation increased DNA uptake and transfection efficiency may help us to modify current pre-transfection approaches in order to reach similar enrichments of transfection efficiency.

Staining the media-conditioned differentiating ES cells for F-actin revealed presence of cross fibers in the replated and non serum-starved cells. In the serum-starved differentiating ES cells, the cells were larger in size, which may have increased the probability of lipoplex/cell membrane interaction, and the presence of actin was localized around the nucleus and cell membrane, suggesting a disrupted F-actin network as a result of serum starvation, which may have reduced the tension of the plasma membrane, thus leading to an expanded plasma membrane and cell size (Lenne et al., 2006; Raucher and Sheetz, 1999B; Raucher and Sheetz, 2000; Titushkin and Cho, 2006; Titushkin and Cho, 2007). This expanded membrane may have lead to an increased endocytosis rate (Raucher and Sheetz, 1999A). The presence and formation F-actin fibers appeared to resume when serum-starved cells were transfected with Cy3 oligonucleotides and assessed after 10 minutes. This rapid stimulation of stress fibers was detected in a study on serum-starved Swiss 3T3 cells to occur as early as two minutes after serum-containing media was added (Ridley and Hall, 1992). The actin cytoskeleton is believed to play an important role in clathrin-mediated endocytosis, the main internalization mechanism believed to be employed by Lipofectamine™ 2000 (Colin et al., 2000; Douglas, 2008; Hoekstra et al., 2007; Yarar et al., 2005). Proteins involved in the nucleation step of actin filament polymerization are implicated in the formation of endocytic vesicles (Engqvist-Goldstein and Drubin, 2003; McPherson, 2002; Merrifield 2004; Munn, 2001). Thus, newly forming and extending actin filaments as cells recover from the serum starvation may help push endocytic vesicles from the plasma membrane.

An additional endocytic mechanism by which serum starvation may have increased DNA uptake and transfection efficiency could be the induction of macropinocytosis, or the intense engulfment of extracellular fluid. It has been shown that macropinocytosis can take place in cells that do not naturally phagocytose, and this phenomena is linked to growth factor stimulation (Jones, 2007). Macropinocytosis depends on signaling to the actin cytoskeleton and utilizes an actin-driven mechanism to protrude the plasma membrane and engulf large volumes of fluid in macropinosomes (Amyere et al., 2002; Nakase et al., 2007). This manifests as membrane ruffles and can be induced with growth factors to occur within 5 min (Nakase et al., 2007). A decrease in membrane-cytoskeleton adhesive forces may occur in parallel with increased rates of fluid phase endocytosis (Raucher and Sheetz, 2001). Additional investigations are needed in the form time-lapse images to assess for the formation of membrane ruffling upon transfection in our media-conditioned cell populations.

The original motivation for exploring improvements in transient gene delivery was to increase the yield of differentiating ES cells expressing the Cyp7A1 reporter vector. We surprising found that not only did the cells continue to proliferate under serum-starvation conditions (albeit at a slower rate than normal media-treated cells), but that the number of cells expressing the Cyp7A1 reporter plasmid vector increased 2.4-fold, as compared to the control replated cells. This translates into a near 10-fold yield in cells available for recovery following sorting. Endocytosis and nucleocytoplasmic shuttling of endocytic proteins are believed to be independent processes. However, some endocytic proteins do play a role in transcriptional regulation (Vecchi et al., 2001). An increased presence of endocytic proteins upon transfection of the serum-starved cells, irrespective of the type of endocytosis, may have led to the increased expression of the Cyp7A1 reporter population.

When serum starving the Hepa 1-6 and NIH3T3 cells, we found that transfection efficiencies after three days decreased as compared to the replated cells. The Cy3 oligonucleotide model was accurate in predicting this decline. The decrease may be due to the fact that both cell types exhibit properties of immortalization or that the depletion of serum from 10% to 0.5% may not be as critical as the drop from 20% to 0.5% in the differentiating ES cells. We did note that there was insignificant difference in average cell areas between the two media conditioned Hepa 1-6 cells, while the serum-starved differentiating ES cells were significantly larger than their non serum-starved counterparts. Furthermore, we did not optimize the length of the serum starvation conditioning in these cells, as was the case in the differentiating ES cells, so we cannot conclusively exclude these cells from being subject to serum starvation-dependent transfection enhancement. Through additional optimization, it may be possible to increase DNA uptake and transfection efficiency in these cells as well.

The methods developed in these studies have the capacity to improve gene delivery to and expression in differentiating stem cells and can be extended to delivery of essentially any gene or bioactive agent of interest without undue experimentation. Such bioactive agents include, but are not limited to any nucleic acid expressing an amino acid sequence which is desirable to express within a cell, or any nucleic acid sequence to express another nucleic acid (e.g. siRNA) or any nucleic acid which is desirable to incorporate into a genome (e.g. sequences for knockouts or transgenic mouse models). To this end, the bioactive agent of the present invention may be any nucleic acid sequence which is used as a template for a protein, a template for an RNA interference agent, a genetic material for preparation of transgenic/knockout organisms, or similar molecular mechanism which are known in the art. With adaptation, the methods described herein are applicable to other mature, somatic cells as well. Delivering genetic vectors through non-viral plasmids is amenable to safer and clinically-sited manufacturing practices, and developing efficient systems for completing this task will make scale-up feasible and transferable to industrial cellular engineering systems.

EXAMPLES

Methods and Materials

Example 1

Cell Culture

The ES cell line D3 (ATCC, Manassas, Va.) was maintained in an undifferentiated state in T-75 gelatin-coated flasks (Biocoat, BD-Biosciences, Bedford, Mass.) in Knockout Dulbecco's Modified Eagles Medium (Gibco, Grand Island, N.Y.) containing 15% knockout serum (Gibco), 4 mM L-glutamine (Gibco), 100 U/mL penicillin (Gibco), 100 U/mL streptomycin (Gibco), 10 µg/mL gentamicin (Gibco), 1000 U/mL ESGRO™ (Chemicon, Temecula, Calif.), 0.1 mM 2-mercaptoethanol (Sigma-Aldrich, St. Louis, Mo.). ESGRO™ contains leukemia inhibitory factor (LIF), which prevents embryonic stem cell differentiation. Every 2 days, media was aspirated and replaced with fresh media. Cultures were split and passaged every 5-6 days, following media aspiration and washing with 6 mL of phosphate buffered solution (PBS) (Gibco). Cells were detached following incubation with 3 mL of trypsin (0.25%)-EDTA (Gibco) for three min, resulting in a single cell suspension, followed by the addition of 12 mL of Knockout DMEM. Cells were then replated in gelatin-coated T-75 flasks at a density of $1 \times 10^6$ cells/mL.

In order to induce differentiation, cells were suspended in Iscove's Modified Dulbecco's Medium (Gibco) containing 20% fetal bovine serum (Gibco), 4 mM L-glutamine (Gibco), 100 U/mL penicillin, 100 U/mL streptomycin (Gibco), 10 µg/mL gentamicin (Gibco). Embryoid bodies were formed and cultured for three days using the hanging drop method (1000 ES cells per 30 µl droplet). Hanging drops where transferred to suspension culture in 100 mm petri dishes and cultured for an additional day. The EBs were then plated, one EB per well, in 12-well tissue culture polystyrene plates (BD-Biosciences) for an additional 13 days. EB cells were detached following incubation with 0.5 mL of trypsin-EDTA (Gibco) for three min, resulting in a single cell suspension, and neutralized by the addition of IMDM media. Cells were then replated in 12-well tissue culture treated polystyrene plates (BD-Biosciences) at an initial seeding density of $5 \times 10^4$ day 17 cells per well for further analysis. These cells are hereby referred to as day 17 differentiating ES cells. Culture medium was changed every 2-3 days.

The Hepa 1-6 cell line (ATCC, Manassas, Va.) and NIH3T3 fibroblasts (a gift from Dr. Li Kim Lee) were maintained in Dulbecco's Modified Eagles Medium (Gibco) containing 10% fetal bovine serum (Gibco), 100 U/mL penicillin (Gibco), 100 U/mL streptomycin (Gibco), and 4 mM L-glutamine (Gibco). Hepa 1-6 and NIH3T3 fibroblast cells were grown on tissue culture treated T-75 flasks (Falcon, BD Biosciences, San Jose, Calif.).

All cell cultures were incubated in a humidified 37° C., 5% $CO_2$ environment

Example 2

Cloning of Albumin Enhancer/Promoter and Cytochrome P450 7α1 (Cyp7A1) Promoter into pDsRedExpress1 Vector The pDsRedExpress1 plasmid vector was attained from BD Biosciences Clontech (Mountain View, Calif.). The cytochrome P450 7α1 (Cyp7A1) vector was donated in the form of a PGL3-Promoter vector from Dr. Gregorio Gil (Virginia Commonwealth University, Richmond, Va.). The promoter region was excised at a blunt and a sticky end and inserted via ligation into a respective blunt and sticky site in the parent pDsRedExpress1 vector. Correct insertion of the regulatory segment into the pDsRedExpress1 vector was confirmed by screening bacterial clones via test transfections in mouse Hepa 1-6 cells and by DNA sequencing up- and down-stream of both insertion sites. This vector is hereby referred to as pCyp7A1-DsRedExpress1. An additional vector, pDsRed2-C1, driven by the constitutive cytomegalovirus immediate early promoter, was used as a control for positive transfection and sorting of the differentiating ES cells.

Example 3

Selection of Cy3 Oligonucleotide

The Cy3 fluorescently-tagged oligonucleotide was obtained from Integrated DNA Technologies (Coralville, Iowa). The 20-base sequence modified at the 5' end with a Cy3 fluorescent dye consisted of random oligonucleotides selected for each base. The GC content of the oligonucleotide as reported by the manufacturer was 51.6%.

Example 4

Particle Size and Zeta Potential Measurements

In order to evaluate the physicoelectrical properties of the DNA lipoplexes, we characterized both the particle size and zeta potential of the two DNA lipoplexes: the Cy3 oligonucleotide/Lipofectamine™ 2000 complex and the plasmid DNA/Lipofectamine™ 2000 complex after 20 min of particle complex formation. The solutions were diluted in Opti-MEM reduced serum media (Invitrogen) at an equivalent volume that would be added to a cell culture well and analyzed using a Brookhaven Particle Size and ZetaPALS Analyzer (Holtsville, N.Y., USA). The ratio of µg DNA:µL reagent carrier was preserved in both complexes. For the plasmid DNA, we used the pDsRed2-C1 plasmid, as this vector would be used as a measure of overall transfection efficiency in all cell types tested. We found that the Cy3 oligonucleotide lipoplex particles had a diameter of 716 nm, while the plasmid DNA lipoplex particles had a diameter of 604 nm. The zeta potential of the Cy3 oligonucleotide lipoplex particles was −10.7 mV, and that of the plasmid DNA lipoplex particles was −28.1 mV. By altering the ratio of the DNA: Lipofectamine™ 2000, we could adjust the sizes and zeta potentials of the two lipoplexes and bring them within close range of each other. As the plasmid DNA: Lipofectamine™ 2000 ratio was optimized in prior work for delivery to differentiating ES cells, we sought to conserve this ratio for Cy3 oligonucleotide lipoplex introduced in this study (Wallenstein et al., 2008). The size and zeta potential differences between the Cy3 oligonucleotide lipoplex and the plasmid DNA lipoplex did not hamper its function as a predictive model of DNA uptake.

Example 5

Transient Transfection of Differentiating Stem Cells, Hepa 1-6 Cells and NIH3T3 Fibroblast Cells The liver-specific expression vector, pCyp7A1-DsRedExpress1, along with the constitutive pDsRed2-C1 plasmid, were transiently transfected using Lipofectamine™ 2000 (Invitrogen, Carlsbad, Calif.) into the differentiating stem cells into the replated and media-conditioned differentiating stem cells. Only the pDsRed2-C1 vector was transfected into the replated or media-conditioned Hepa 1-6 and NIH3T3 fibroblast cells. A DNA: Lipofectamine™ 2000 ratio of 0.8 µg DNA: 1.0 µL reagent was used in a 48-well plate. This ratio was conserved and amounts adjusted as per the manufacturer's protocol for different sized well plates. The transfection complexes were prepared and delivered in serum-free Opti-MEM Reduced-Serum media (Invitrogen, Carlsbad, Calif.) and replenished with normal serum-containing media after 4 h. Visual cell confluency of cells at the time of transfection was maintained in the 40-70% surface coverage range (FIG. 9).

Example 6

Serum Starvation and Sample Collection

The EBs were trypsinized and replated in IMDM media containing 20% FBS. The control population consisted of cells transfected with the Cy3 oligonucleotides or the reporter plasmids as early as possible after replating (within 4-12 h). Experimental conditions for media conditioning were initiated by replating cells for 4-12 h in 20% FBS-containing IMDM media, removing the media and replenishing these cells with IMDM media containing 0.5% FBS (serum-starved condition) or 20% FBS (normal media) for 1, 2 and 3 days, after which they were immediately transfected with the Cy3 oligonucleotides or the reporter plasmids. Hepa 1-6 and NIH3T3 fibroblast cells were plated in DMEM media containing 10% FBS. The control population (cells replated for 4-12 h) were transfected with the Cy3 oligonucleotides or the reporter plasmids. Media-conditioned Hepa 1-6 cells and NIH3T3 cells were replated for 4-12 h, at which point the media was removed and replenished with DMEM media containing 0.5% FBS (serum-starved condition) or 10% FBS (normal media) for an additional 3 days. After 3 days, they were immediately transfected with the Cy3 oligonucleotides or the reporter plasmids.

Cells transfected with the Cy3 oligonucleotides were trypsinized at 12 min, 24 min and 36 min after addition of the complexes, and fluorescent activity/particle uptake was determined via flow cytometry. Cells transfected with the reporter plasmids were trypsinized following 36-48 h, and red fluorescent activity/transfection efficiency was detected via flow cytometry and imaged using a computer-interfaced inverted Olympus IX70 microscope.

Example 7

Flow Cytometry and Cell Sorting

The BD FACSCalibur™ (San Jose, Calif.) system is a four-color, dual-laser, benchtop system capable of both cell analysis and sorting. To quantify DsRed expression, cell medium was aspirated, cells were washed with PBS and trypsinized for 1 min and resuspended in PBS. Instrument settings were calibrated using mock transfected and non-transfected cells. Cells were then analyzed using dot plots measuring forward versus side scatter and FL-3 (red fluorescence) versus FL-1 (green fluorescence), as well as histogram plots measuring count values of FL-1 and FL-3. Using the flow cytometry values as described above, the region of interest was then selected for the cell sort gating threshold. Sorted lines were cleansed with 70% ethanol and buffered with sterile PBS. Positive-gated cells were collected in tubes that were pre-incubated in cold FBS. Tubes were centrifuged at 950 RPM for 7 min, and cells were replated in IMDM differentiation medium. The yield of cells recovered in each sort was approximately 80% of the number of cells gated and counted by the flow cytometer. Media was replenished after approximately 4-5 h after the sort to remove any additional contaminants or debris remaining once the sorted cells adhered to the cell culture plates. The cells to be assessed for cytochrome P450 detoxification function were treated with 3-methylcholanthrene for 48 h.

Example 8

Sandwich ELISA for Detection of Albumin Secretion

Media samples were collected directly from cell cultures at the specified time points and stored at −20° C. for subsequent analysis. Albumin secretion was detected using a commercially available kit (Bethyl Laboratories, Montgomery, Tex.). Anti-albumin capture antibody was diluted 1:100 in coating buffer and 100 µL was added to each well of a 96-well Nunc-Immuno MaxiSorp plate (NUNC, Denmark). The plates were incubated for 1 h at 37° C. followed by three washes. This was followed by the addition of 200 µL of blocking solution and 30 min incubation at 37° C. The plate was washed three times and 100 µL of standards and samples were added to their respective wells. The plate was incubated for 1 h at 37° C. and washed three times. A horseradish peroxidase conjugated anti-mouse albumin antibody was diluted 1:10,000 and 100 µL was added to each well, incubated for 1 h at 37° C. and washed five times. An o-phenylene-diamine (OPD) (Sigma-Aldrich) substrate solution was prepared, 100 µL was added to each well and incubated for 15 min at room temperature. The reaction was stopped by the addition of 100 µL 2M $H_2SO_4$. Absorbance readings were obtained using a Bio-Rad Model 680 plate reader (Hercules, Calif.) with a 490 nm emission filter. A standard curve was generated by creating serial dilutions of albumin standard from 7.8 ng/mL to 10,000 ng/mL and a linear fit of the standards was used to determine the albumin concentration in each sample.

Example 9

Urea Secretion

Media samples were collected directly from cell cultures at the specified time points and stored at −20° C. for subsequent analysis for urea content. Urea secretion was assayed using a commercially available kit (StanBio, Boerne, Tex.). Urea enzyme reagent (100 µL) was added to each well of a 96-well plate followed by addition of 10 µL of standards/samples to the enzyme reagent. The plates were centrifuged at 1,000 RPM for 1 min and then placed in a water bath at 37° C. for 5 min. Urea color reagent (100 µL) was then added to each well followed by centrifugation and water-bath incubation. Absorbance readings were obtained using a Bio-Rad Model 680 plate reader (Hercules, Calif.) with a 585 nm emission filter. A standard curve was generated by creating serial dilutions of a urea standard from 0 µg/mL to 300 µg/mL and a linear fit of the standards was used to determine the urea concentration in each sample.

Example 10

Measurement of Cytochrome P450 Activity

Cytochrome P450 activity was induced by treatment with 3-methylcholanthrene (2 µM) (Sigma-Aldrich) for 48 h prior to the activity assay. Cytochrome P450-dependent resorufin o-dealkylase activity was measured using resorufin substrates methoxyresorufin (MROD) from a Resorufin Sampler Kit (Invitrogen, Carlsbad, Calif.). The incubation mixture contained the methoxyresorufin substrate (5 mM) and dicumarol (80 mM) in phenol red free Earle's Balanced Salt Solution (EBSS) (Gibco). The prepared solutions were preheated to 37° C. prior to incubation with cells. The 12-well plates were washed with 2 mL of EBSS (37° C.) and further incubated with 2 mL of EBSS at 37° C. for 5-7 min, to remove the residual medium. Following removal of EBSS, the incubation mixture was added (2 mL per well), and the dishes were incubated at 37° C. in a 5% $CO_2$ incubator. At various time points (10, 20, 30, 40 min) following incubation, 100 µL of the mixture was transferred into a 96-well plate. The fluorescence of the plate was measured using a DTX880 fluorescence plate reader (Beckman Coulter, Fullerton, Calif.) with an excitation of 530 nm and emission of 590 nm. A standard curve of resorufin fluorescence was constructed at each time point using concentrations ranging from 1 to 1,000 nmol in EBSS. Linear curves were obtained with an $r^2 \geq 0.98$. The constructed standard curves were used to convert the fluorescence values obtained from the plate reader to nanomoles of resorufin. Rate of formation of resorufin, as calculated from the early linear increase in the fluorescence curve, was defined as cytochrome P450 activity and expressed as pmol/cell/min.

Example 11

F-Actin Visualization and Determination of Cell Area

A rhodamine-phalloidin F-Actin Visualization Biochem Kit™ was obtained from Cytoskeleton, Inc. (Denver, Colo.). Cells were washed with wash buffer for 30 s, fixed with a formaldehyde-based fixative solution for 10 min, washed for 30 s, permeabilized for 5 min and washed for another 30 s, all at room temperature. Samples were stained with the rhodamine-phalloidin dye for 30 min at room temperature in the dark. Cells were washed three times with the wash buffer and with PBS. Actin filaments were then visualized via fluorescence microscopy (excitation filter 525 nm; emission filter 585 nm) using an inverted Olympus IX70 microscope and a confocal Olympus IX81 microscope. To determine two-dimensional cell area, at least 10 cells were selected from three distinct fluorescent images of each respective condition using the Olympus Microsuite™ software. Cell regions of interest (ROIs) were defined by manually encircling cell membranes. The ROIs were then detected using the software, and the particle results yield cell area values in pixel$^2$ units.

Example 12

Apoptotic DNA Detection

An Apoptotic DNA Ladder Kit was obtained from Roche Diagnostics (Indianapolis, Ind.) to detect the presence of apoptotic or necrotic cell death. At each point examined for cell death due to serum starvation cells were trypsinized, diluted in PBS, centrifuged and frozen at −20° C. until analysis. At the time of analysis, binding/lysis buffer was added to the cell pellet and a positive control from the kit (lyophilized apoptotic U937 cells), vortexed for 5-10 s and incubated for 10 min at room temperature. Isopropanol was added to this solution, vortexed briefly, and the solution was placed in a collection column. The column was centrifuged for 1 min at 8000 RPM on table top centrifuge to bind the nucleic acids to the filter. The filter was washed and the sample eluted. The samples, positive control and 100 bp and 1 kb ladders were run through a 1% agarose tris-borate EDTA (1×) gel containing ethydium bromide for 50 min at 110 V. The gel was then visualized and a digital image printed using a UV Transilluminator (UVP, Upland, Calif.). Apoptotic samples are indicated by a non-random fragmentation "ladder pattern" of DNA on the gel. Necrotic samples are indicated by a randomly digested DNA smear. Non-necrotic and non-apoptotic cells are indicated by a single band comprising the entire genomic DNA.

Example 13

Statistical Analysis of Measurements

Each data point represents the mean of three or greater experiments (each with biological triplicates), and the error bars represent the standard deviation of the mean. Statistical significance was determined using the Student's t-test for unpaired data. Differences were considered significant if the P-value was less than or equal to 0.05.

Results

Example 14

Effect of Serum Starvation on Uptake of Cy3 Oligonucleotides

The fluorescence of the Cy3 oligonucleotide lipoplex particles facilitiated rapid quantification, via flow cytometry, of the percentages of cells that acquired the DNA. Murine ES cells differentiating in EBs were trypsinized at 17 days of differentiation. To assess the effect of serum changes at different time points, we explored seven experimental groups. The control group consisted of cells that were replated for 4-12 h and then transfected immediately. To assess the effects of long-term "media conditioning", six additional groups of cells consisted of cells that were replated for 4-12 h after trypsinization and then replenished with either IMDM media containing 20% FBS or IMDM media containing 0.5% FBS for 1, 2 and 3 days. For each experimental condition, Cy3 oligonucleotides were transfected into the cells in Opti-MEM serum-free media. Cells were sampled at 12 min after addition of the Cy3 oligonucleotide lipoplexes (FIG. 1). The three serum-starved cell groups indicated a presence of Cy3 oligonucleotides in 40-70% of the cells, while the cells treated with normal media contained particles in less than ~15% of the cells. The condition with the greatest particle uptake was the 3-day serum-starved condition. The control cell population that was transfected immediately after replating without media conditioning had uptake levels of ~40%.

Example 15

Correlation of Cy3 Oligonucleotide Uptake to CMV Plasmid Transfection Efficiency with Media Conditioning Next, we explored the correlation of the Cy3 oligonucleotide uptake rates to the transfection efficiency of the constitutive CMV plasmid. The seven experimental groups described above (i.e., control, serum-starved for 1, 2 and 3 days, and normal media for 1, 2, and 3 days) were transfected with pDsRed2-C1 plasmid DNA complexed with Lipofectamine™ 2000 for 4 h in Opti-MEM media as described in the Methods and Materials section. After 48 h, the number of fluorescent cells was quantified via flow cytometry (FIG. 2A). Compared to the control replated ES cell group, which had an efficiency of ~50% of the total cell population, the transfection efficiency of the normal media-treated populations decreased with each subsequent day of incubation, with the 3-day non serum-starved group showing the lowest efficiency (~28%). In contrast, the serum-starved populations all increased in transfection efficiency, when compared to the replated population, with the greatest efficiency noted in the 3-day serum-starved group (~83%). Cells serum-starved for 4 or 5 days were not transfected as significant cell death (above 10%) became apparent beyond 3 days as did the diminishment of hepato-specific functions (data not shown).

Example 16

Cyp7A1 Expression Rates with Media Conditioning

Once we established that serum starvation could improve transfection efficiency of a constitutively-expressed CMV promoter-driven plasmid, we sought to determine if these conditions would enhance the expression of a liver-specific Cyp7A1 promoter-driven plasmid. The control and media-conditioned differentiating ES cell groups were transfected with the pCyp7A1-DsRedExpress1 plasmid and assessed in a manner identical to that of the pDsRed2-C1 plasmid transfection (FIG. 2B). We found that with respect to the replated ES cell population, which had an expression rate of ~1.5%, the serum-starved groups increased in the 1- and 3-day treatment case but not in the 2-day case, with the greatest expression noted at 3 days of serum starvation (~3.7%). The cells treated with normal media for 1-3 days all had decreased levels of Cyp7A1 expression, with the lowest noted after 2 days (~0.49%). As mentioned above, we did not test Cyp7A1 reporter expression on cells beyond the 3-day serum starvation point due to loss of basal function.

Example 17

Use of the Cy3 Oligonucleotide Model to Predict Transfection Efficiency in Serum Starvation of Other Cell Types To determine if the serum starvation media conditioning could be applied to other cell types and whether the Cy3 oligonucleotide model could be used to predict such trends, we explored the media conditioning of Hepa 1-6 mouse hepatoma cells and NIH3T3 mouse fibroblasts. Based on the Cy3 oligonucleotide model, both three-day serum-starved and non serum-starved groups of Hepa 1-6 cells demonstrated less DNA uptake than that of the replated Hepa 1-6 control cells (P<0.05) (FIG. 3A). In parallel, the transfection efficiency of the Hepa 1-6 cells was lower in the serum-starved (P<0.01) and non serum-starved (P<0.05) conditions as compared to the replated Hepa 1-6 control cells (FIG. 3B). For the NIH3T3 fibroblasts, the Cy3 oligonucleotide uptake for the serum-starved cells was lower than that of the replated control cells (P<0.05) (FIG. 3C). Similarly, the CMV plasmid transfection efficiency of 3-day serum-starved NIH3T3 cells was lower than the replated control cells (P<0.05) (FIG. 3D).

Example 18

F-Actin Staining of Media-Conditioned Cells

In an effort to understand the intracellular changes that accompany serum starvation, we examined the presence and structure of F-actin in the media-conditioned differentiating ES cells and Hepa 1-6 cells.

We stained the cells with a rhodamine-phalloidin dye and compared four groups: differentiating ES replated fixed after 4 hours; differentiating ES serum-starved for three days and fixed; differentiating ES serum-starved for three days, transfected with Cy3 oligonucleotides and fixed 10 min thereafter; and differentiating ES cells fed with normal media for three days and fixed. F-actin fibers were strongly present in cells that were replated (FIG. 4A) and in cells treated with normal media for three days (FIG. 6D). However, minimal F-actin staining was noted for the serum-starved cells (FIG. 4B). When transfected with Cy3 oligonucleotides in Opti-MEM media and fixed after 10 min, F-actin fibers appeared to be restored (FIG. 6C). We used the F-actin staining images to compare the two-dimensional cell area of the media-conditioned differentiating ES cells and the Hepa 1-6 cells (FIG. 5). We found that the differentiating ES cells serum-starved for three days showed greater average area than the cells treated with normal media (P<0.05). In the three-day media-conditioned Hepa 1-6 cells, however, both groups showed similarly-sized cell areas. Therefore, the effect of serum starvation on all transfectability occurs concomitantly with F-actin ultrastructural changes.

Example 19

Functional Evaluation and Proliferative Ability of Cells During and Following Media Conditioning To ascertain whether media conditioning led to apoptosis or necrosis in the media-conditioned cells, we performed a DNA ladder test where genomic DNA extracted from cell lysates of all treatment conditions were run on a gel electrophoresis (FIG. 6). In the event of apoptosis, the genomic DNA would produce step bands in its lane. In the event of necrosis, the genomic DNA would smear across the lane. All media-conditioned treated cells produced one solid band which did not migrate below the highest 1 kb DNA ladder step ladder band, indicating neither apoptosis nor necrosis was induced in any treatment condition. A positive control sample is shown in lane B producing step bands.

We also plotted the cell growth after uniform plating in a 12-well plate after 6 hours and after 1, 2 and 3 days of media conditioning (FIG. 7). Cells treated with 20% FBS-containing media grew at a quicker rate than the serum-starved cells. At all test points, negligible number of cells appeared to be detached and less than 5% of the cells were dead as determined by Trypan blue exclusion staining. At 4 and 5 days of serum starvation, the number of dead cells in each sample exceeded 10% of the population. Despite the fact that growth rate is reduced following serum starvation, as compared to normal media-treated cells, the yield of recoverable cells that were positively transfected increased nearly 10-fold following three days of serum starvation [i.e., 3321 cells (3.69% of 90,000 3-day serum-starved cells) compared to 337 cells (1.53% of 22,000 replated cells)].

Finally, we evaluated the effect of media conditioning on the functional capacity of the differentiating ES cells. We sorted the cells after three days of media conditioning (with both normal 20% FBS media and serum-starved 0.5% FBS media) using both the CMV and the Cyp7A1 reporter plasmids. The CMV plasmid was used as a control plasmid for the cell sort. The Cyp7A1 plasmid was used as a liver-specific reporter to target the hepatocyte-like subpopulation of differentiating ES cells. Cells were assessed for urea secretion, albumin secretion and Cyp1A2 detoxification functions (FIGS. 8A-C). For all three assays, the media conditioning showed no significant enhancement or decrement between the serum-starved and non serum-starved groups. The Cyp7A1-sorted cells were significantly enriched (P<0.05) from their CMV-sorted counterparts in all three functional assays.

We claim:
1. A method for delivering a non-viral plasmid vector to a differentiating embryonic stem cell comprising:
  culturing a differentiating human or murine embryonic stem cell in a serum starved condition for about 1 to about 3 days,
  delivering to the cell cultured in the serum starved condition a non-viral plasmid vector encoding and capable of expressing a bioactive agent; and
  expressing the bioactive agent within the differentiating embryonic stem cell.
2. The method of claim 1 wherein the cell is a differentiating human embryonic stem cell.

3. The method of claim 2 further comprising the step of isolating the embryonic stem cell from an embryoid body prior to the culturing step.

4. The method of claim 1 wherein the cells are cultured on IMDM media having 0.5% or less of fetal bovine serum.

5. The method of claim 1 wherein the cell is a differentiating murine embryonic stem cell.

\* \* \* \* \*